(12) United States Patent
Martinez et al.

(10) Patent No.: US 12,354,728 B2
(45) Date of Patent: Jul. 8, 2025

(54) BUILDING MEALS BASED ON INGREDIENTS ON HAND AND DIETARY NEEDS

(71) Applicant: Bia Studios LLC, Brooklyn, NY (US)

(72) Inventors: Erik Martinez, Brooklyn, NY (US); Daniel Papadimitropoulos, Brooklyn, NY (US)

(*) Notice: Subject to any disclaimer, the term of this patent is extended or adjusted under 35 U.S.C. 154(b) by 178 days.

(21) Appl. No.: 17/369,244

(22) Filed: Jul. 7, 2021

(65) Prior Publication Data

US 2022/0013213 A1    Jan. 13, 2022

Related U.S. Application Data

(60) Provisional application No. 63/049,317, filed on Jul. 8, 2020.

(51) Int. Cl.
| | |
|---|---|
| G16H 20/60 | (2018.01) |
| G06Q 10/0834 | (2023.01) |
| G06Q 30/0601 | (2023.01) |
| H04W 4/02 | (2018.01) |

(52) U.S. Cl.
CPC ....... *G16H 20/60* (2018.01); *G06Q 10/08345* (2013.01); *G06Q 30/0633* (2013.01); *H04W 4/023* (2013.01)

(58) Field of Classification Search
CPC .... G16H 20/00; G16H 20/60; G06Q 10/0834; G06Q 30/0633
USPC .......................................................... 705/2
See application file for complete search history.

(56) References Cited

U.S. PATENT DOCUMENTS

| | | | |
|---|---|---|---|
| 2006/0199155 A1* | 9/2006 | Mosher | G16H 20/60 434/127 |
| 2009/0075242 A1* | 3/2009 | Schwarzberg | G09B 19/0092 434/127 |
| 2009/0275002 A1* | 11/2009 | Hoggle | G16H 20/60 707/999.1 |

FOREIGN PATENT DOCUMENTS

WO    WO-2019148019 A1 *   8/2019  ....... G06F 16/90324

OTHER PUBLICATIONS

Zhang, Donglan; Impact of Different Policies on Unhealthy Dietary Behaviors in an Adult Population of Los Angeles County: An Agent-Based Simulation Model; University of California, Los Angeles. ProQuest Dissertations Publishing, 2014. 3621458. (Year: 2014).*

* cited by examiner

*Primary Examiner* — Hiep V Nguyen
(74) *Attorney, Agent, or Firm* — Taft Stettinius & Hollister LLP

(57) ABSTRACT

A system for building a meal includes: a processing device configured to generate a meal based on user health data and dietary data; a communications link connecting a client computing device to the processing device for transmitting the user health data and dietary data; a food database containing an archive of food ingredients and nutritional data; and randomly-generated meal data having a subset of ingredients and nutritional facts for each ingredient in said subset. The processing device has a sub-meal randomization generator to randomly select a sub-meal based on a signal indicative of a meal type selected from the client computing device, and an ingredients randomization generator to access the food database, filter the archive of food ingredients based on the dietary data to determine a set of ingredients, and randomly select from the set of food ingredients said subset of ingredients based on the sub-meal.

19 Claims, 19 Drawing Sheets

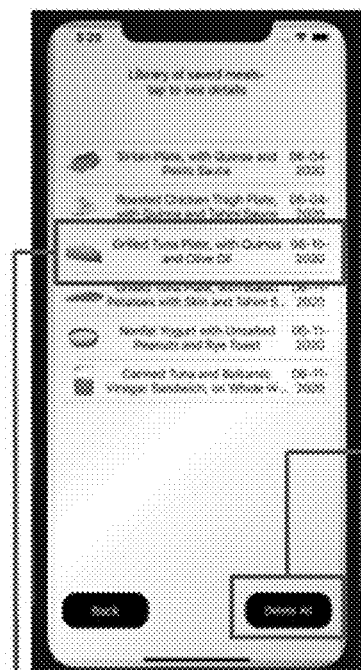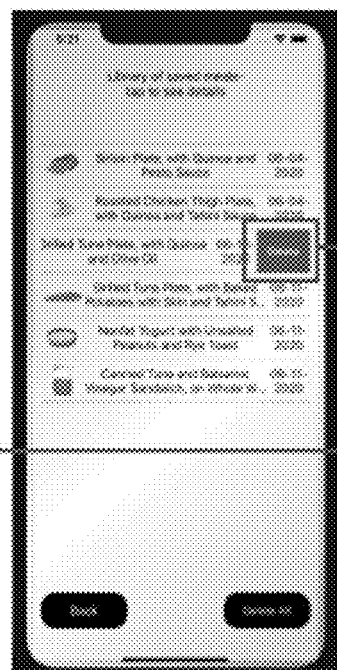
FIG. 3D

| Food Name | Serving (quantity) | Serving (units) | Calories | Fat (grams) | Calories from Fat | Saturated Fat (grams) | Trans Fat (grams) | Cholesterol (mg) | Sodium (mg) | Carbohydrates (grams) |
|---|---|---|---|---|---|---|---|---|---|---|
| Low Fat Yogurt | 2 | oz | 38.5 | 1 | 8.25 | 0.5 | 0 | 3.75 | 42.75 | 4.25 |
| Nonfat Yogurt | 2 | oz | 32 | 0 | 0 | 0 | 0 | 0 | 25 | 2 |
| Nonfat Cottage Cheese | 0.5 | cup | 52 | 0 | 0 | 0 | 0 | 5 | 270 | 5 |
| Oatmeal | 0.5 | cup | 71 | 1 | 10 | 0 | 0 | 0 | 5 | 13 |
| Shredded Wheat | 0.5 | cup | 86 | 1 | 10 | 0 | 0 | 0 | 1 | 20 |
| Milk | 1 | cup | 103 | 2.4 | 20 | 1.5 | 0 | 12 | 107 | 12 |
| Almond Milk | 1 | cup | 30 | 2.5 | 20 | 0 | 0 | 0 | 170 | 1 |
| Soy Milk | 1 | cup | 33 | 1.7 | 15 | 0.3 | 0 | 0 | 9 | 1.6 |
| Grapefruit | 0.5 | grapefruit | 52 | 0 | 0 | 0 | 0 | 0 | 0 | 13 |
| Orange | 0.5 | medium orange | 31 | 0 | 0 | 0 | 0 | 0 | 0 | 9 |
| Banana | 6 | inch | 90 | 0 | 0 | 0 | 0 | 0 | 1 | 19 |
| Blackberries | 0.5 | cup | 37.33 | 0 | 0 | 0 | 0 | 0 | 0 | 9.33 |
| Blueberries | 0.5 | cup | 42 | 0 | 0 | 0 | 0 | 0 | 0.5 | 11 |

FIG. 4A

| Food Name | Sugar (grams) | Fiber (grams) | Protein (grams) | Category | Gluten Allergy | Dairy Allergy | Shellfish Allergy | Peanuts Allergy | Vegetarian | Image Identifier |
|---|---|---|---|---|---|---|---|---|---|---|
| Low Fat Yogurt | 4.25 | 0 | 3.25 | Breakfast Yogurt | N | Y | N | n | N | Yogurt |
| Nonfat Yogurt | 2 | 0 | 6 | Breakfast Yogurt | N | Y | N | N | N | Yogurt |
| Nonfat Cottage Cheese | 1 | 0 | 7 | Breakfast Yogurt | N | Y | N | N | N | Cottage Cheese |
| Oatmeal | 0 | 2 | 2 | Breakfast Cereal | Y | N | N | N | N | Oatmeal |
| Shredded Wheat | 0 | 3 | 3 | Breakfast Cereal | Y | N | N | N | N | Shredded Wheat |
| Milk | 13 | 0 | 8 | Breakfast Milk | N | Y | N | N | N | Milk |
| Almond Milk | 0 | 0.7 | 1 | Breakfast Milk | N | N | N | Y | N | Milk |
| Soy Milk | 0.6 | 1.1 | 3.5 | Breakfast Milk | N | N | N | Y | N | Milk |
| Grapefruit | 8 | 2 | 1 | Breakfast Fruit | N | N | N | N | N | Grapefruit |
| Orange | 6 | 1.5 | 0.5 | Breakfast Fruit | N | N | N | N | N | Orange |
| Banana | 6 | 2 | 1 | Breakfast Yogurt Fruit | N | N | N | N | N | Banana |
| Blackberries | 3.33 | 4 | 0.67 | Breakfast Yogurt Fruit | N | N | N | N | N | Blackberry |
| Blueberries | 7.5 | 2 | 0.5 | Breakfast Yogurt Fruit | N | N | N | N | N | Blueberry |

FIG. 4B

```
struct FoodStruct{ var FoodName: String
    var Serving_Qty: String
    var Serving_Units: String
    var Calories: String
    var Fat_Grams: String
    var Calories_from_Fat: String
    var Saturated_Fat_Grams: String
    var Trans_Fat_Grams: String
    var Cholesterol_mg: String
    var Sodium_mg: String
    var Carbohydrates_Grams: String
    var Sugar_Grams: String
    var Fiber_Grams: String
    var Protein_Grams: String
    var Category: String
    var GlutenAllergy: String
    var DairyAllergy: String
    var ShellfishAllergy: String
    var PeanutsAllergy: String
    var Vegetarian: String
    var Image_Identifier: String

```
func MealCal()->Double{ var mealCal: Double = 0 if IM == "Breakfast"{
        mealCal = DC*0.225
    }
    if IM == "Lunch"{
        mealCal = DC*0.225
    }
    if IM == "Dinner"{
        mealCal = DC*0.3
    } return mealCal
}
```

```
//Breakfast Sandwich Egg
var breakfastSandwichEggBread:[FoodStruct] = []
var breakfastSandwichEggProtein:[FoodStruct] = []
var breakfastSandwichEggAddition:[FoodStruct] = []
var breakfastSandwichEggAddition2:[FoodStruct] = []
var breakfastSandwichEggSide:[FoodStruct] = []
```

FIG. 8G

```
//Size up the Addition
breakfastSandwichEggAddition2[0].Serving_Qty =
    String(round(10*((Double
    (breakfastSandwichEggAddition2
    [0].Serving_Qty) as!
    Double)*breakfastSandwichAddition2Multiplier)
    )/10)
breakfastSandwichEggAddition2[0].Calories =
    String(round(10*((Double
    (breakfastSandwichEggAddition2[0].calories)
    as!
    Double)*breakfastSandwichAddition2Multiplier)
    )/10)
breakfastSandwichEggAddition2[0].Fat_Grams =
    String(round(10*((Double
    (breakfastSandwichEggAddition2[0].Fat_Grams)
    as!
    Double)*breakfastSandwichAddition2Multiplier)
    )/10)
```

As can be seen here, the serving quantity, calories, and fat grams (other nutritional infor is sized the same exact way) simply have their base nutritional values that are associated with them in the raw data multiplied by the multiplier computed above, so that they reflect the correct values for the quantity of that ingredient actually included in the meal

FIG. 8I

```
@IBAction func Reload(_ sender: UIButton) {
    var mealReloaded = MealRandomizer(reducedMasterList,
        mealType, DC, IM)
```

FIG. 8J

```
if mealType == "Breakfast_Sandwich_Egg"{ if locationsForRerunTruncated[2] == 0{ breakfastSandwichEggAdditionString[0] =
            (String("\(calories)
            \(mealReloaded[2].Calories)"))
        breakfastSandwichEggAdditionString[1] =
            (String("\(fatGrams)
            \(mealReloaded[2].Fat_Grams)"))
        breakfastSandwichEggAdditionString[2] =
            (String("\(calFromFat)
            \(mealReloaded[2].Calories_from_Fat)"))
        breakfastSandwichEggAdditionString[3] =
            (String("\(saturatedFat)
```

FIG. 8K

BUILDING MEALS BASED ON INGREDIENTS ON HAND AND DIETARY NEEDS

TECHNICAL FIELD

The present teachings relate generally to interactive mobile health devices and applications, and more specifically to a system, method, and application which prepares nutritional or diet recommendations based on user feedback of accessible ingredients and prevailing dietary preferences.

BACKGROUND

A person's overall health is shaped by a number of factors. Genetic profile, medical history, fitness activity, environment, nutrition, and diet all affect a person's overall health and wellness. Obesity, or excess weight, is considered an epidemic and has been growing at an increasing rate. Cardiovascular diseases, diabetes, and other health disorders are similarly growing. One of the main reasons, if not the primary reason, for the increasing trends in health complications is poor nutrition and diet.

Numerous nutritional programs have been offered to the public over the years. Most of the programs designed for losing weight rely on limiting food intake based on one or more criteria, such as calories, carbohydrates, etc. Some examples of weight loss programs are the Atkins diet (Atkins Nutritionals, Inc.), the South Beach diet, the Zone diet, Ketogenic diet, Weight Watchers diet, and Mediterranean diet. In addition, there are fitness applications and mobile software that provide different exercise routines and track user workouts. Other health applications monitor user weight loss and track daily carbohydrate intake. Nevertheless, these conventional applications do not assist users with achieving a healthy diet conducive for weight loss. The biggest drawback with these known applications is that they require substantial amounts of user data entry, such as entering the total time spent exercising (e.g., walking, running, swimming, rowing), the total distance traveled, the number of sets and repetitions of particular exercise motions, the weight of dumbbells, the kind and amount of food eaten by the user during a particular meal, the total calorie consumption for a meal, the total number of meals and/or snacks the user had in one day, the volume of liquids drank by the user in one day, etc. The effort and time needed to enter all necessary data, especially on a daily basis, for optimal use of the applications end up irritating users and may result in discontinued or intermittent usage of the applications. Alternatively, users may skip data entries, thereby providing inaccurate or incomplete history of the user's progress.

Nutrition applications for mobile devices currently help with grocery shopping, for example allowing a user to scan barcodes to quickly pull up nutritional information about food products. Other applications offer users recipes, articles and advice from health experts. The recipes include nutritional facts and can be modified with respect to serving size. However, these known applications assume that the user readily has at hand the required ingredients to make the recommended recipe. This is not always the case since most users engage with their health applications at the moment they need or want to utilize them. For instance, a user may open up a known nutritional recipe application when s/he is in the kitchen ready to begin preparing a meal. The user may not have the time or convenience to go to the grocery store to purchase any missing ingredients. Furthermore, some recipes require certain cookware and kitchen utensils that the user does not have. Known applications are not flexible or responsive to these issues and may not allow for user modification or adaptation to prevailing circumstances. The overall effect is that the user may cease use of the nutrition application or skip the recommended recipe and opt for a less healthy meal, both of which detract from the ultimate goal of better health.

In some instances, conventional health applications have issues with information overload, which is a situation where too much information is pushed on to the user who has limited processing abilities towards the information. Research has shown that a person performs diverse information-related activities on a mobile device using an ever-growing range of applications. As the number of activities (applications) increases, the person will feel overwhelmed by the amount of information flooded to the mobile device, thereby causing mental stress. This may ultimately lead to the person discontinuing use of an application (e.g., health application) or using the application sparingly. Such outcome essentially renders the health application ineffective. Additionally, it is known that the average Internet user's attention span is around 8 seconds. The 8-second attention span is also true for health applications. If applications provide content requiring more than 8 seconds of attention, the user is less likely to finish reading or viewing the content, and instead abandon the application. This is especially true for nutrition applications based on the operational principle of providing full recipes and multi-step cooking instructions.

Thus, there exists a need for an improved health system, method, and application that overcomes the drawbacks related to excessive user data entry, information overload, and inflexibility to a user's prevailing or real-time conditions, as well as other issues with prior art health applications.

SUMMARY

The needs set forth herein as well as further and other needs and advantages are addressed by the present embodiments, which illustrate solutions and advantages described below.

It is an object of the present teachings to remedy the above drawbacks and shortcomings associated with known health systems and applications.

In particular, it is an object of the present teachings to provide a health system that is simple and requires minimal data entry by the user, as well as a corresponding method and application.

It is another object of the present teachings to provide a health system, method, and application which provide a flexible weight-loss regimen tailored to a user's nutritional goals and dietary restrictions, and more specifically provides an ingredients list from which a user can create a meal or snack according their preferred method of preparation or cooking.

It is also an object of the present teachings to provide a health system, method, and application that build a meal (e.g., breakfast, lunch, dinner, afternoon snack, pre-workout snack, post-workout snack, etc.) with high nutritive value based on ingredients that the user has on hand and that pair well together in terms of flavor, taste, and/or manner of preparation.

It is a further object of the present teachings to provide a health system, method, and application that allow users to exclude ingredients (which the users do not have currently in the kitchen or pantry) and/or include ingredients (which the users have currently in the kitchen or pantry). The health system, method, and application accordingly can reconstruct an ingredients list based on the exclusion and/or inclusion while maintaining one or more nutrient parameters at a minimum threshold necessary for reaching the user's nutritional goals.

It is another object of the present teaching to provide a health system, method, and application that implements a graphical user interface designed to showcase nutritional information, caloric content, and/or serving size information in a brief, concise form for each component within the built ingredients list so that the information may be easily understood and "digested" by the user. The present teachings seek to provide a health system, method, and application that presents easily digestible content related to ingredients for building a nutritious meal.

These and other objects of the present teachings are achieved by providing a nutrition system or application that seeks to enhance weight loss through dieting. Using a particular module and/or algorithm with specific formulas to estimate daily caloric intake, the system or application randomly generates different meals compiled from random ingredients based upon user inputs and desires. The system obtains information related to a user's allergies, current weight, desired weight, time period in which the user wishes to lose the weight (or possibly gain healthy weight), and a meal type (e.g., breakfast, lunch, dinner, afternoon snack, pre-workout snack, post-workout snack, etc.). Based on the results of one or more randomization generators/functions, a meal is randomly selected from a list of ingredients that correspond with the meal. The system or application provides user control to either re-randomize the entire meal or certain ingredients of the meal, or save the meal to a library (linked to the user's profile) for later viewing. These meals are based on estimated nutrition computations and information, and serve as ideas and guidelines for the user to either consume as is, or alter during their meal preparation or cooking. The system or application is flexible in that it allows for users to adjust and customize meals so that they include only ingredients that the users have on hand in their current location (e.g., kitchen or pantry) and to choose the method of preparation or cooking.

More specifically, the present teachings provide a system for building a meal, which comprises a processing device configured to generate a meal based on user health data and dietary data, a client computing device positioned at a user location, a communications link connecting the client computing device to the processing device for transmitting the user health data and dietary data, a food database containing an archive of food ingredients and nutritional data, and randomly-generated meal data comprising a subset of ingredients and nutritional facts for each ingredient in said subset. The processing device has a sub-meal randomization generator and an ingredients randomization generator, wherein the sub-meal randomization generator is configured to randomly select a sub-meal based on a signal indicative of a meal type selected from the client computing device, wherein the ingredients randomization generator is configured to access the food database, filter the archive of food ingredients based on the dietary data to determine a set of ingredients, and randomly select from the set of food ingredients said subset of ingredients based on the sub-meal. The processing device retrieves the nutritional facts from the nutritional data stored in the food database and compiles the randomly-generated meal data for transmission to the client computing device.

The processing device may further comprise a module configured to compute a daily calorie intake based on the user health data, said module allocates a portion of the daily calorie intake for the meal type selected from the client computing device based on fixed proportions. The processing device determines the number of ingredients to include in the subset of ingredients according to the randomly-selected sub-meal. Additionally, the processing device applies predefined percentages to the allocated portion of the daily calorie intake to determine an amount of calories to be allotted to each subset ingredient, wherein upon determining the amount of calories to be allotted to each subset ingredient, the processing device uses a multiplier to calculate the serving size for each subset ingredient to be included in the meal.

The objects of the present teachings are also achieved by providing a system for building a meal, which comprises a processing device configured to generate a meal based on user health data and dietary data, a client computing device positioned at a user location, a communications link connecting the client computing device to the processing device for transmitting the user health data and dietary data, a food database containing an archive of food ingredients and nutritional data, and randomly-generated meal data comprising a subset of ingredients and nutritional facts for each ingredient in said subset. The processing device has a sub-meal randomization generator and an ingredients randomization generator, wherein the sub-meal randomization generator is configured to randomly select a sub-meal based on a signal indicative of a meal type selected from the client computing device, wherein the ingredients randomization generator is configured to access the food database, filter the archive of food ingredients based on the dietary data to determine a set of ingredients, and randomly select from the set of food ingredients said subset of ingredients based on the sub-meal. The processing device is also configured to transmit an order signal to an external service platform for purchasing one or more of the subset of ingredients or a meal having at least a majority of the subset of ingredients.

Americans struggle with weight issues and constantly seek weight loss aids. The nutrition system and application according to the present teachings provide a way for the user to potentially lose weight (or gain healthy weight) and meet a weight loss (or weight gain) goal. The randomization generators or functions (which can re-randomize) provide a way for the user to choose a meal of preference to meet weight goals, as opposed to a pre-chosen meal that is issued. This is an advantage because the method behind weight loss/dieting is different from competitors, and the user has a different level of control over what meal they eat via the randomizers. The user can thus choose a meal type that they like as opposed to a meal type issued. The randomization generators or functions will always generate a meal from the user's preferences. The features of the system enable users to reach a goal weight more efficiently since they will be eating meals for which they have a preference and desire. Many individuals tend to be indecisive when trying to come up with something healthy to eat, and as such, often end up settling on an unhealthy option or an option unconducive to their nutritional goals. The present teachings attempt to prevent such adverse outcome.

Other features and aspects of the present teachings will become apparent from the following detailed description, taken in conjunction with the accompanying drawings, which illustrate by way of example the features in accordance with embodiments of the present teachings. The summary is not intended to limit the scope of the present teachings.

BRIEF DESCRIPTION OF THE DRAWINGS

FIGS. 3A-3D are exemplary screenshots of a meal-building system and/or application according to the present teachings.

FIGS. 4A-4B show an exemplary data table of foods and corresponding nutritional information utilized by a meal-building system and/or application according to the present teachings.

FIGS. 8A-8K show exemplary processing modules of a meal-building system and/or application according to the present teachings.

DETAILED DESCRIPTION

The present teachings are described more fully hereinafter with reference to the accompanying drawings, in which the present embodiments are shown. The following description illustrates the present teachings by way of example, not by way of limitation of the principles of the present teachings.

The present teachings have been described in language more or less specific as to structural features. It is to be understood, however, that the present teachings are not limited to the specific features shown and described, since the product herein disclosed comprises preferred forms of putting the present teachings into effect.

Figure 1:
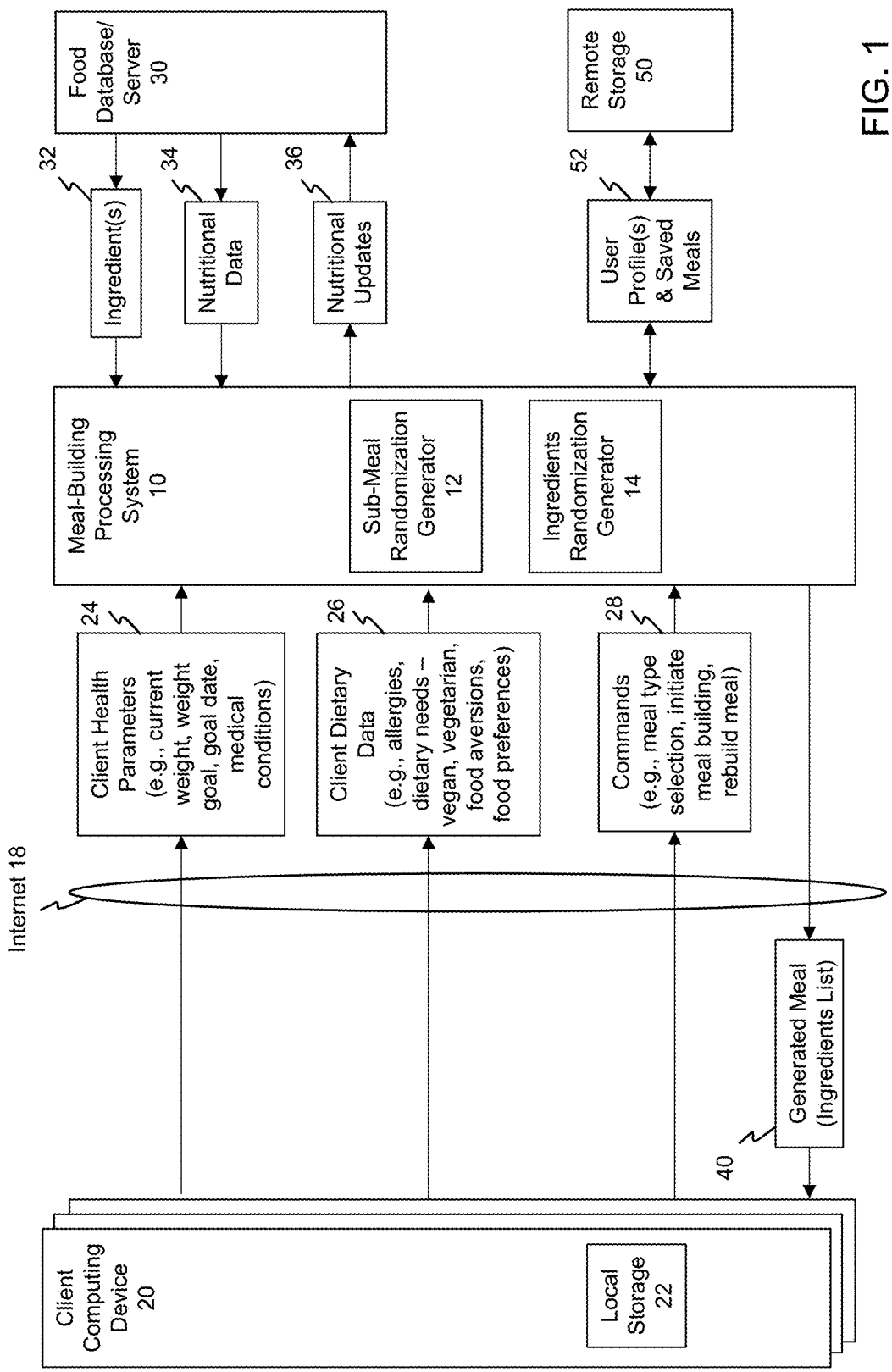
FIG. 1 is a block diagram of a meal-building system and/or application according to the present teachings.

FIG. 1 is a block diagram of a nutrition system or application that seeks to enhance weight loss (or healthy weight gain) through dieting. In particular, the system provides a randomly-generated ingredients list to a client computing device for making a nutritious meal tailored to a user's current health (e.g., current weight), dietary needs (e.g., allergies, food aversions, food preferences) and goals (e.g., desired weight, desired date). Using formulas to estimate daily caloric intake, the system randomly generates different meals compiled from random ingredients based upon user inputs and desires. The user indicates allergies, current weight, desired weight, time period in which they wish to lose the weight (or possibly gain healthy weight), and meal type (e.g., breakfast, lunch, dinner, afternoon snack, pre-workout snack, post-workout snack, etc.). Based on the results of one or more randomization generators or modules (e.g., randomizer function(s)), a meal is randomly selected from a list of ingredients that correspond with the meal. In some embodiments, the randomization generators or modules may comprise, be built upon, and/or be based on a randomizer or a hardware-based random number generator. The system enables the user to then choose to either re-randomize the entire meal or certain ingredients of the meal. The system includes remote storage and/or local storage configured to save the meal to a library for later viewing. These meals are based on estimated nutrition computations and information, and are adapted to serve as ideas and guidelines for the user to either consume as is, or alter during meal preparation.

As shown in FIG. 1, one or more client computing devices 20 are connected to the meal-building processing system or application 10 by an Internet communications link 18. In some embodiments, the client computing devices may be connected to the meal-building processing system via various wireless communications technologies, such as but not limited to WiFi, Bluetooth, radio communications, or satellite communications. In other embodiments, the client computing devices 20 and the meal-building processing system 10 transmit and receive data through a cable (e.g., Ethernet cable). Although not shown, in some instances, the meal-building processing system or application 10 may be embodied within the client computing device 20, such that these components form one physical device.

The meal-building processing system 10 may include a processor, a computer, a server, or some other type of processing device. It comprises a hardware-based randomizer(s) and/or a software-based randomizer(s), such as algorithms, designed specifically for generating personalized meals for users, including a sub-meal randomization generator 12 and an ingredients randomization generator 14. The system 10 obtains user health data 24 from the client computing device 20, such as but not limited to current weight of the user, the user's weight goal (e.g., a weight less than the current weight or greater than the current weight), the user's desired date for achieving the weight goal, and/or medical conditions (e.g., bloating, heartburn, constipation, nausea, irritable bowel syndrome, etc.). In some cases, the user health data 24 may involve information or measurements of the user's recent physical activity. For example, system 10 may retrieve data regarding the number of steps and/or miles traveled by the user in the past hour (or some other predefined period of time), which is measured by the client computing device 20 (e.g., mobile device, smart watch, wearable technology, and/or the like). In addition, the system 10 collects information from the client computing device 20 concerning the user's dietary needs and restrictions. For example, client dietary data 26 may include but is not limited to allergies (e.g., milk-lactose, eggs, nuts, peanuts, shellfish, wheat, gluten, soy, fish, etc.), food preferences (e.g., vegetarian, vegan, pescatarian, etc.), and/or food aversions (e.g., dislike taste or texture of certain foods). Upon receiving the user's health data/parameters 24 and dietary data 26, the system 10 is configured to receive commands 28 from the client computing device, including the type of meal selected (breakfast, lunch, dinner, afternoon snack, pre-workout snack, post-workout snack). The commands 28 may also include a signal from the client computing device to initiate a meal building process and/or to rebuild a previously generated meal.

When the meal-building processing system 10 receives the initiate meal-build command, it proceeds to determine a meal based on the health parameters 24, the dietary data 26, and commands 28 (i.e., meal type selected) by initializing the randomizer(s) or randomization generator(s) and starting one or more corresponding algorithms designed to generate a completely random meal idea. More specifically, through a graphical interface on the client computing device 20, the user may click a button that starts the algorithm(s) to generate a randomized meal with each individual ingredient randomly generated by the randomizer. A function begins by computing the number of calories that the user must consume daily based on their current and goal weight, as well as time-frame inputs, then splits that daily calorie amount by meal (e.g., breakfast, lunch, and dinner) based on fixed proportions (e.g., Breakfast is 22.5% of daily calories, Lunch is 22.5% of daily calories, and Dinner is 30% of daily calories, with the rest being available for snacking and beverages throughout the day). In other embodiments, the system may be configured to implement other meal proportions, for example, one arrangement involving two major meals per day or another involving six smaller meals spread throughout the day. Preferably, the system offers a plurality of daily meal arrangements from which the user may select, at which point the system configures itself by utilizing the algorithms that calculate appropriate meal proportions. Once the meal is determined, the randomizer(s) will randomly select from a list of "sub-meals". For instance, if the chosen meal is breakfast, the system via the sub-meal randomization generator 12 will randomly select breakfast sandwich, breakfast cereal, or breakfast yogurt among others as the sub-meal. The sub-meal randomization generator 12 will access and retrieve an array of foods 32 and their nutrition information 34 from the food database or server 30, which serves as raw data for the system. This raw data is then filtered down based on allergy, food aversions, and food preferences from user inputs (i.e., dietary data 26), as well as its suitability for the meal that is being generated. The sub-meal randomization generator 12 comprises algorithms which then allocate the portion of the meal calories that will go to each individual ingredient, such as the protein or the carbohydrates. The connection between the system 10 and the server 30 may be established for example via a PHP (hypertext preprocessor) backend that connects to a MySQL server. It is also noted that the system 10, or some other external system, may provide nutritional updates 36 to the server 30. For example, as nutritional research further develops and more accurate or current information concerning nutritional aspects of a food become available, the server 30 is updated to incorporate this information.

The algorithm contained within the system meal-building processing system 10, such as the sub-meal randomization generator 12, is designed such that different sub-meals have different computations, ingredients and side dishes. Based on these formulae (description thereof is provided below), the system 10 will build a meal from scratch, randomly selecting each ingredient to be included in the sub-meal, utilizing an ingredients randomization generator 14. The serving size of each ingredient is then properly sized and scaled to meet the amount of calories that was allocated to it. The system 10 then generates a meal 40, preferably in a format of a table showing the name of the meal as a whole at the top, and each individual ingredient beneath it, accompanied by an image of each individual ingredient in that respective ingredient's cell. Each cell within the table is expandable to show the nutrition information related to the ingredients and the meal as a whole, so that the user may ascertain how many calories, grams of protein, etc. come from each ingredient. The generated meal 40 is output to the client computing device 20. The table format (as shown in FIG. 3C) is especially designed for easy content digestion by the user and for promoting user attention and utilization of the system.

If the user is provided a meal 40, but dislikes some or all of the ingredients, the user may click an icon to lock specific ingredients and re-generate the unlocked ones, effectively telling the system (e.g., randomizer) to replace those specific ingredients with others. The user may also regenerate the entire meal as a whole if desired.

After the system 10 generates a meal with ingredient content that satisfies the user, the system may save the meal to a library that sorts the meals by date. The system is configured to allow the user to retrieve previously saved meals as well as delete meals within a library. The meal may be stored in the client computing device 20 on local storage 22 (e.g., internal hard drive, external hard drive, memory, etc.). For instance, the save functionality may be achieved through X-Code's (Apple's application development system) core data feature. All saved meals will be viewable on the client computing device 20 in table form. In addition or alternatively, the meal may be uploaded to and stored in a remote storage 50. Also, saved meals 52 may be downloaded from the remote storage 50 onto the client computing device 20 for later retrieval and use. Although not shown, the food database/server 30 and the remote storage 50 may comprise one single device in some embodiments.

Figure 2A:
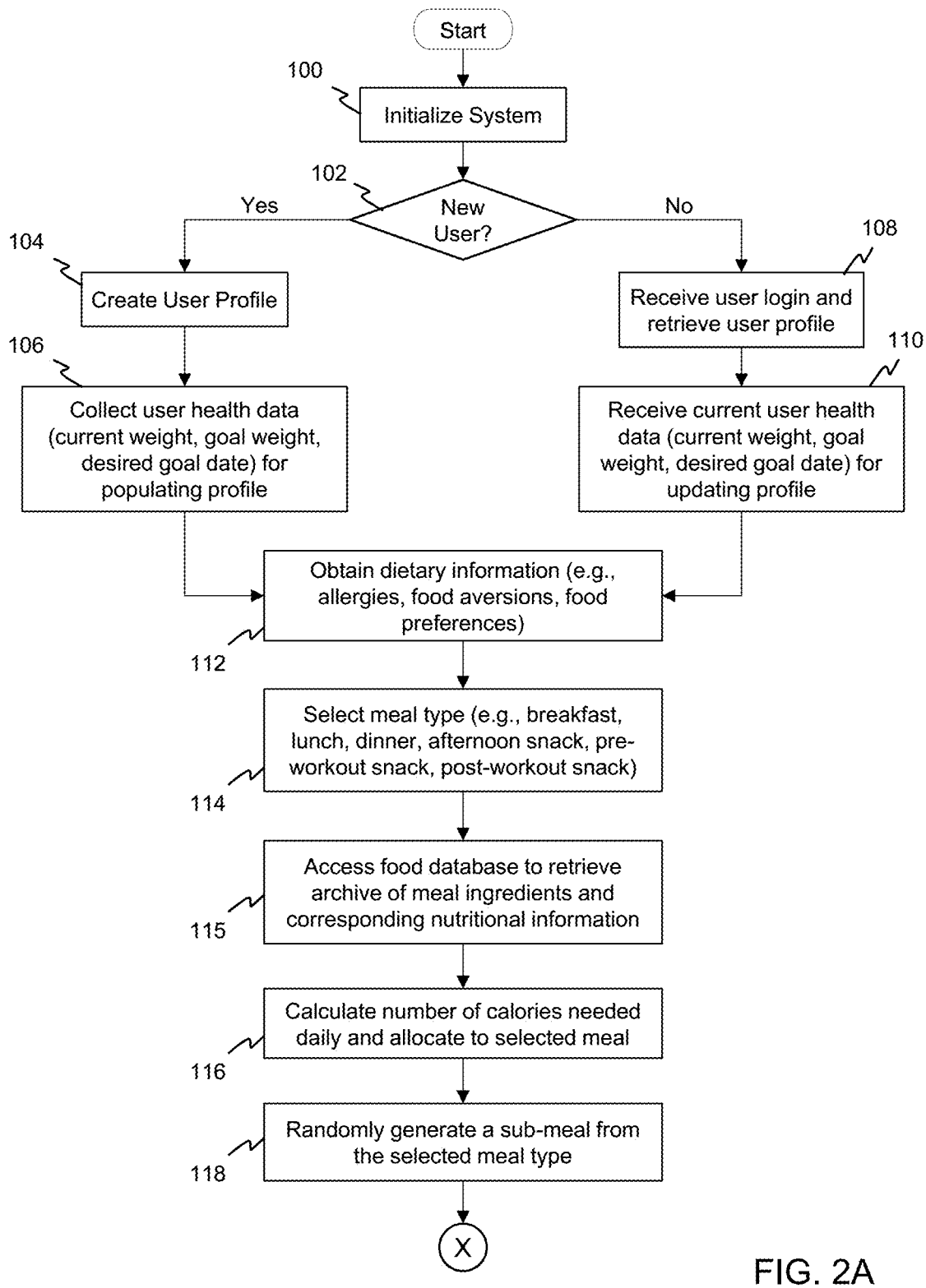
FIGS. 2A-2B depict a flow chart showing a method for building a nutritious meal using a meal-building system and/or application according to the present teachings.
Figure 2B:
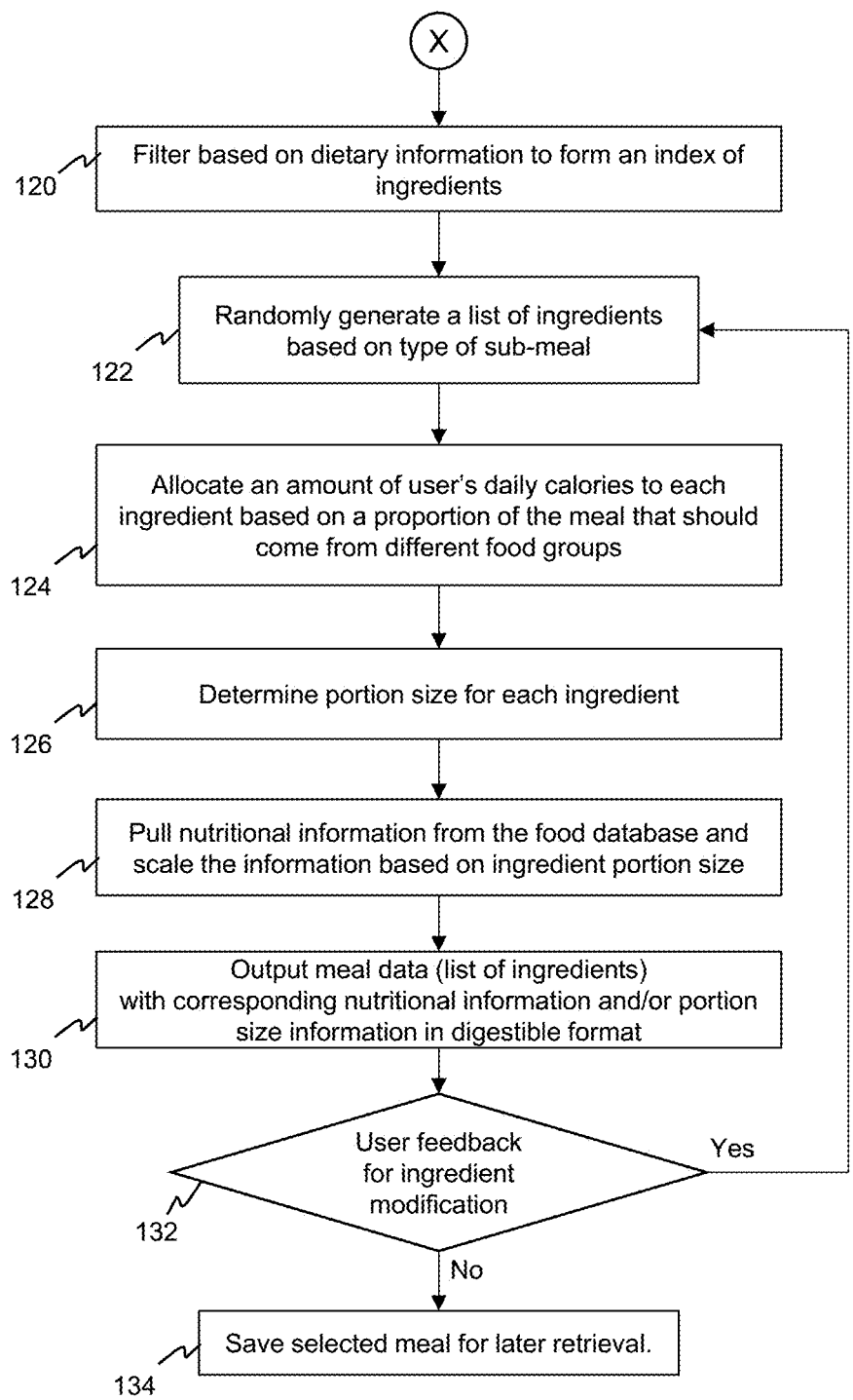

FIGS. 2A-2B show a process for building a nutritious meal using the meal-building system or application of FIG. 1. In step 100, the meal-building system 10 is initialized, for example when the user opens the corresponding program on the client computing device 20. Thereafter, the system determines whether the user is new in step 102. If the user indicates on the client computing device that s/he is a new user, the meal-building system 20 transmits a prompt requesting that the user create a profile 104. The system in step 106 then collects user health data 24, such as but not limited to current weight of the user, the user's weight goal, the user's desired date for achieving the weight goal, and/or medical conditions. This information is used to populate the user's profile. If the user is not new, then the meal-building system 10 in step 108 will prompt the user for login credentials (e.g., username/password; fingerprint ID; facial ID, etc.) in order to retrieve the user's profile from the remote storage 50 for example. The retrieved profile will include previous health data. In step 110, the system 10 receives any current or updated user health data (e.g., current weight, adjusted goal weight, recent physical activity) for updating the user profile.

Thereafter, the system 10 is configured to obtain the user's dietary information 26, including allergy information, food aversions, and/or food preferences, in step 112. Additionally, upon prompting the user through the graphical interface on the client computing device 20, the system 10 in step 114 receives a command 28 in the form of a selection of meal type (e.g., breakfast, lunch, dinner, afternoon snack, pre-workout snack, post-workout snack, etc.). In a step 115, the system 10 accesses the food database/server 30 in order to later receive data regarding list of meal ingredients and corresponding nutritional information. Note, step 115 may be performed later in the process of building the nutritious meal, for example just before step 128. In step 116, the algorithm contained in the system 10 is configured to compute the number of calories needed daily by the user and then allot them to the selected meal based on predetermined percentage of calories intake per meal. Further, the system 10 calculates based on the number of calories needed to gain/lose a certain amount of weight for a given time period. In addition, the system may utilize user health data, for example measurements of user physical activity (within a predefined period of time preceding meal generation), to adjust—either increasing or decreasing—the number of calories to be provided by the selected meal and subsequent meals. In step 118, the system via the sub-meal randomization generator 12 randomly selects a sub-meal. For example, if the user had chosen breakfast as the meal, then the system 10 would randomly select one of a breakfast sandwich, breakfast burrito, yogurt, cereal, oatmeal, hard-boiled egg, avocado toast, etc.

During step 120, the system uses the ingredients randomization generator 14 to filter all the ingredients archived in the food database/server 30 based on the dietary data 26. As a result of the filtering, an index of ingredients is produced. Thereafter in step 122, the ingredients randomization generator 14 randomly selects a list of ingredients from the index of ingredients based on the randomly-selected sub-meal. In some embodiments, the number of ingredients randomly selected may be at least three, preferably five ingredients. However, in other embodiments, the system may be configured such that less than three ingredients are randomly selected. In some instances, the algorithm contained in the system will prompt the user to set the number of ingredients to be randomly selected. It is noted that in some embodiments, the steps of filtering and randomly selecting based on sub-meal may be reversed, such that filtering is performed after random selection. During a step 124, the system allocates an amount of the user's daily calories to that meal component based on proportion of the meal that should come from different food groups (carbohydrates, vegetables, protein, etc.). In step 126, the system algorithm determines a portion size for each of the selected ingredients. In step 128, the system 10 obtains nutritional information (calories, sodium, protein, sugar, etc.) from dataset that is held in the food database/server 30 and scales the information based on ingredient portion size calculated in steps 124 and 126.

Once information is retrieved from the food database/server, the system 10 in step 130 transmits the generated meal (i.e., list of randomly selected sub-meal ingredients which satisfy the user's allergies, food preferences, and/or food aversions) to the client computing device as results. The system 10 renders the generated meal and associated nutritional information (for each ingredient) in a table format. For example, a data table may contain the selected meal with total nutritional facts and each ingredient with corresponding nutritional facts. It has been found that the data format presentation, as shown in FIGS. 3C-3D, allows for quick and easy understanding by the user, i.e., easily digestible content. This data table is transmitted to the client computing device 20 for display.

In some embodiments, the system 10 is configured to provide options to the user to re-randomize the entire meal 40 or certain elements of it in step 132. If the system 10 receives a command requesting re-randomization, steps 120-130 are repeated. The system may also provide a locking mechanism through which one or more of the ingredients listed in the generated meal 40 can be fixed during the re-randomization process. That is, the locked ingredients would remain unchanged during re-randomization, while the other ingredients (i.e., those that are not locked) would be replaced. If the user wishes to save the generated meal (including the list of ingredients and corresponding nutritional facts and portion sizes) for later use and retrieval, the user may engage a save button through the graphical interface, at which point a copy of the generated meal would be stored into local storage 22 (step 134). In some embodiments, the system 10 receives a command from the client computing device 20 to save a copy of the generated meal into remote storage 50. Note, the meal-building system may be arranged so that both the local storage and remote storage save the generated meal, or only of one of them saves the generated meal.

Figure 3A:
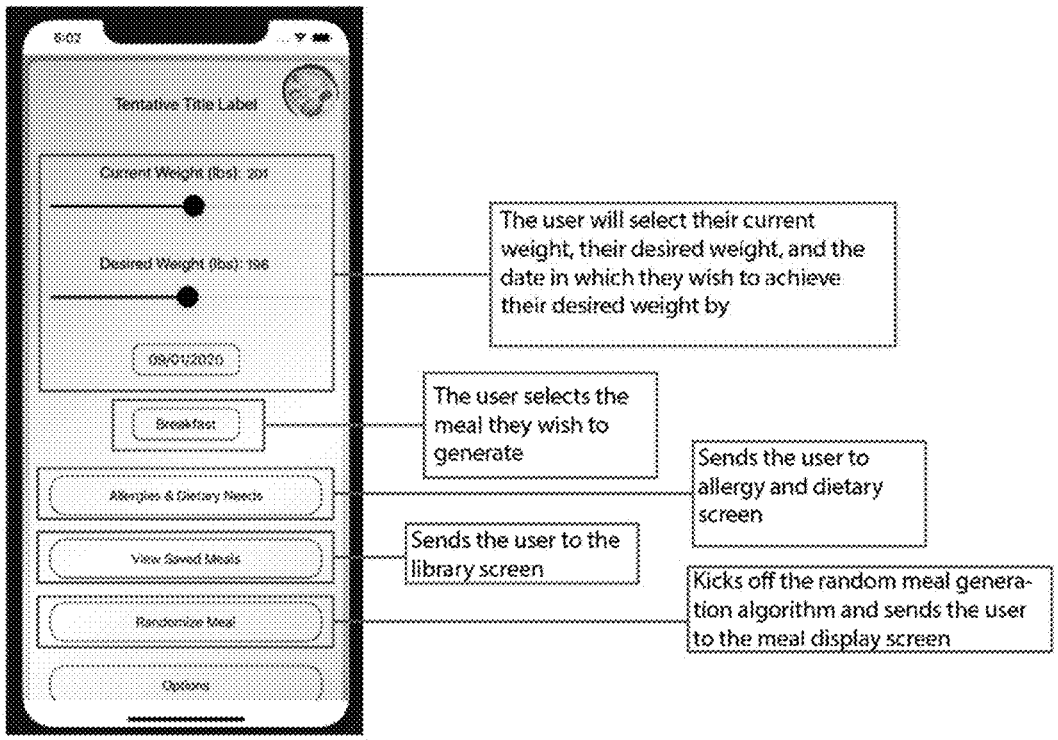
Figure 3B:
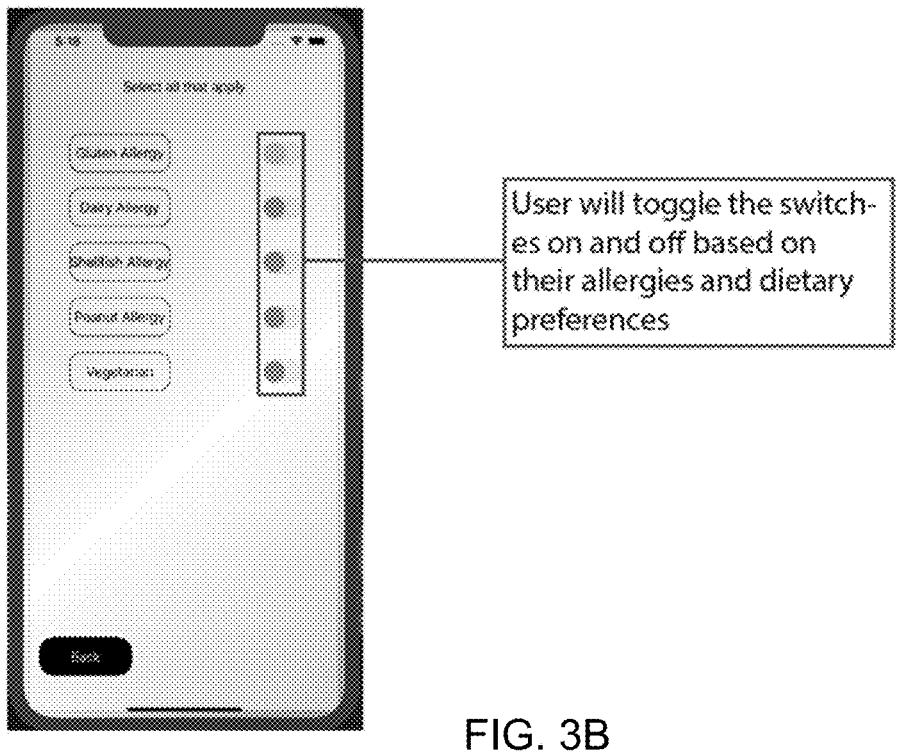
Figure 3C:
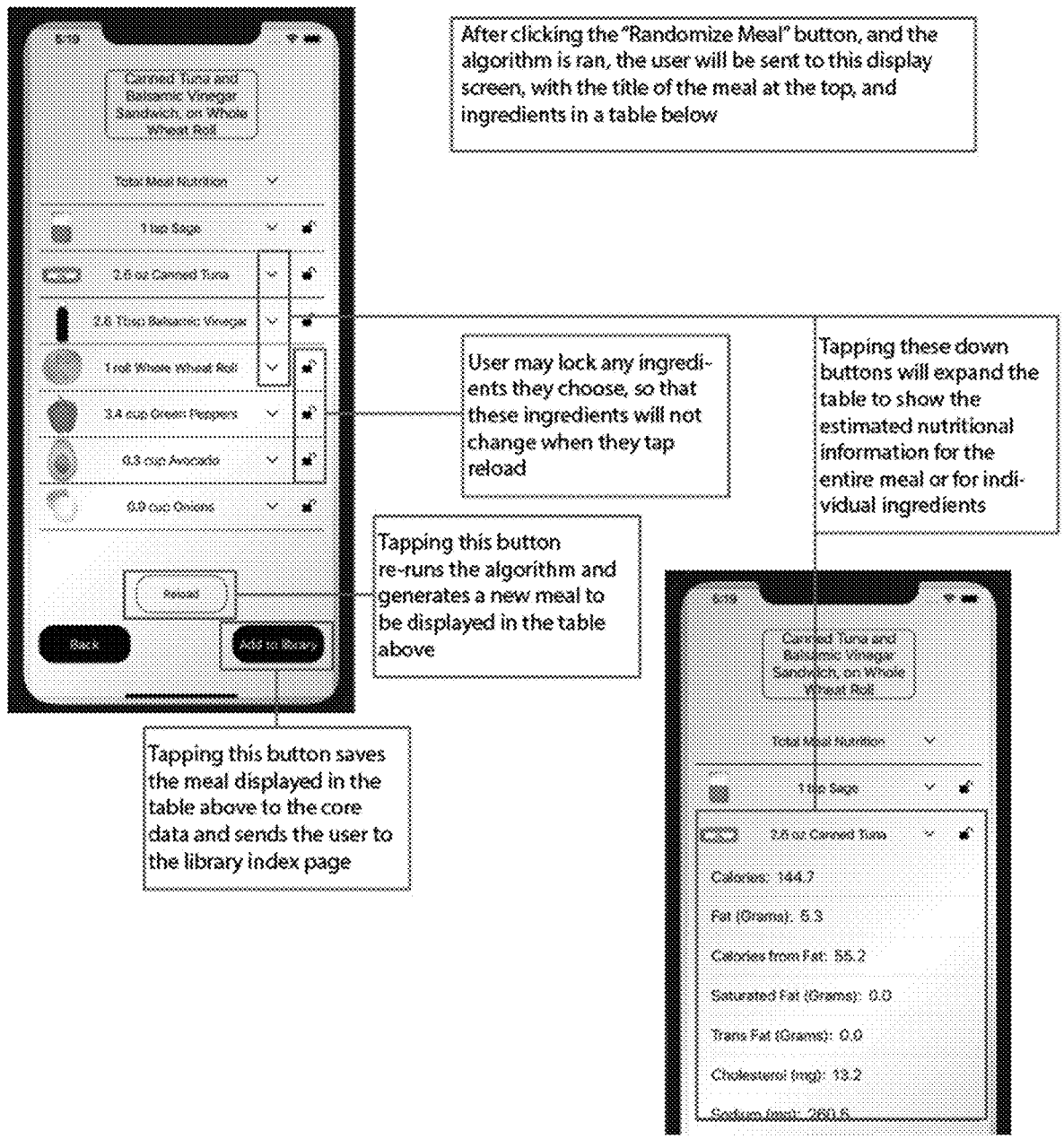

FIGS. 3A-3D show exemplary screenshots of the meal building system or application. On the "Home" page of the graphical interface of the system, a user may indicate a current weight, a desired weight (a weight goal they wish to achieve), the date by which the user wishes to lose said weight, and the meal the user wishes to eat (e.g., Breakfast, Lunch, Dinner, Afternoon Snack, Pre-Workout Snack, Post-Workout Snack). FIG. 3A depicts the Home Screen, and more specifically the parameter fields that the user is able to configure as well as buttons/toggles that will segue the user to different places within the system.

The user may also tap an Allergy and Dietary needs button to be transferred to the "Allergy and Dietary" Screen shown in FIG. 3B, where the user can select or specify allergy(ies) and/or dietary needs that apply to them. This input data may be saved in local storage 22 and/or remote storage 50 under the user's profile so that it may be taken into account and utilized in future operation of the meal-building processing system. The system will remember the state of these switches so that the user does not have to return to this page unless they wish to amend the status of a switch.

After returning to the Home Screen and tapping the "Randomize Meal" button, the system will initialize a randomizer with an algorithm configured to generate a completely random meal idea for the user. The meal is based on estimates to help the user achieve his or her weight loss (or weight gain) goal. The first step of the algorithm is to compute an estimate for the daily calories that the user should take in, in order to meet their goal. In order to estimate this value, the system must first convert the pound values that the user input into kilograms, as shown in FIG. 8A.

Figures 8A, 8B:
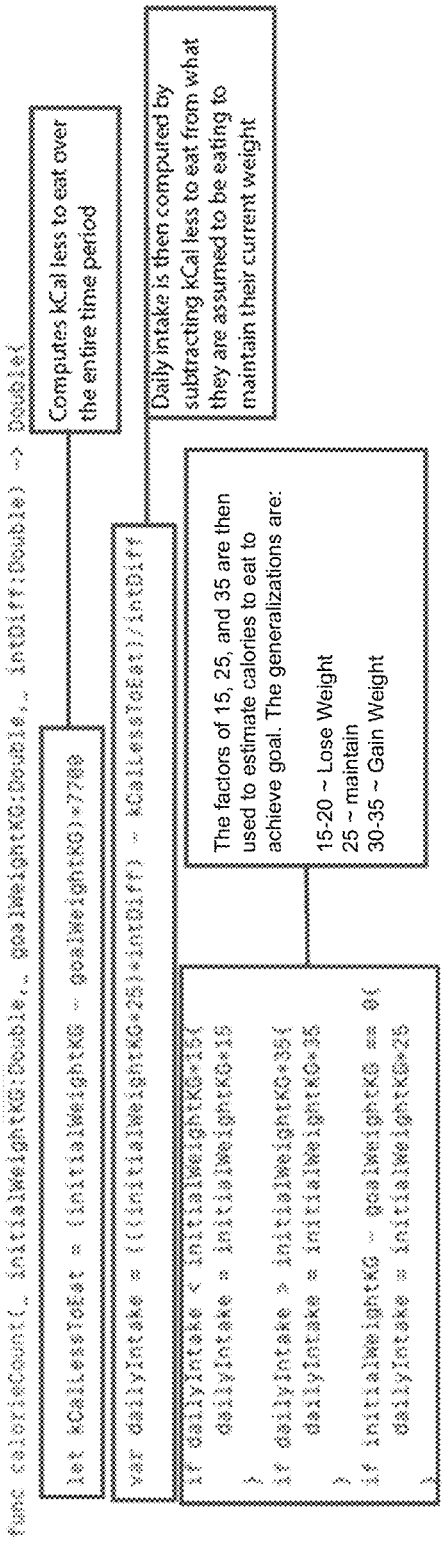

The daily calorie intake is then estimated as shown in FIG. 8B.

The system 10 will access and pull data from the food database or server 30, containing a matrix of hundreds of different food ingredients, their related nutritional information, and other metrics used to filter the data for meal building. One exemplary format of the data, along with a sample of a few rows, is depicted in FIGS. 4A-4B.

Once pulled from the server 30, the data is stored in a matrix of the structure illustrated in FIG. 8C.

Now that the system 10 has computed the estimated daily calories that the user must consume, the meal that the user wishes to eat, the allergy and dietary preferences of the user, and the data pulled from the server, the algorithm will begin construction of the meal. This begins with allocating a portion of the daily calorie estimate to the meal that the user wishes to eat, based on fixed proportions (e.g., Breakfast is 22.5% of daily calories, Lunch is 22.5% of daily calories, and Dinner is 30% of daily calories, with the remaining 25% left available for snacking and beverages throughout the day), such as shown in FIG. 8D.

Figure 9:
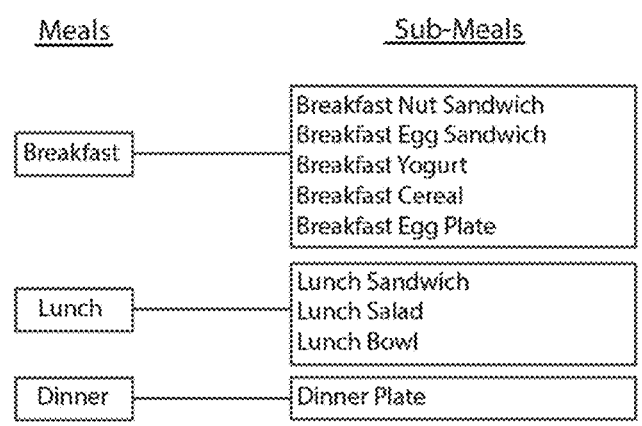
FIG. 9 shows a list of meals and sub-meals.

The system module(s) or algorithm(s) then selects randomly, using the sub-meal randomization generator 12, the type of sub-meal that the system will compile based on the list shown in FIG. 9. Note, the list shown in FIG. 9 is exemplary and is not limited to the specific meals and sub-meals shown. For example, other meal types may include afternoon snack, pre-workout snack, and/or post-workout snack. Other sub-meals may be included, for example ethnic options, wherein if the user wishes to consume dishes originating from a certain part of the world, the user will be served those types of meals, but the following procedures post Sub-Meal selection will remain the same.

The system utilizes a module or algorithm for selecting the Sub-Meal to be constructed. Certain meals, specifically the sandwiches, do not give useable results for people with lower recommended calorie intake (e.g., in an exemplary case, the cutoff is set at 1000 calories), so the system will to attempt to generate those Sub-Meals for people with low calorie intake. One embodiment of this algorithm is shown in FIG. 8E.

Once the sub-meal has been selected, the system 10 begins the data filtering segment of the module or algorithm, where based on the user's allergy and dietary needs, the program will filter the data based on the columns from the raw data entitled "GlutenAllergy", "DairyAllergy", "ShellfishAllergy", "PeanutsAllergy", "Vegetarian", "Vegan", etc. This is done in order to eliminate foods that will conflict with the user's allergy and dietary preferences. The system is configured to provide other allergies and dietary preferences, which the user may select and with which data filtering may be performed. In FIG. 8F, it can be seen that the original data structure, named "ml" is filtered for each allergy or dietary need in a sequential manner, arriving at the final structure, in this case "tempListRed5".

In the next phase, the module or algorithm will begin selecting ingredients for the chosen Sub-Meal from the prior step. Each Sub-Meal has a set structure. For example, a Breakfast Egg Sandwich output will always have 5 components: Bread, Protein, two vegetables, and a fruit on the side, as depicted in FIG. 8G. Each ingredient takes on that same structure (FoodStruct) that the raw data takes when it is pulled from the server, since it contains the same information, just for one ingredient. Note the screenshot just defines the empty arrays for each ingredient in the specific meal (each meal's ingredients are defined just like this), which will be filled in the steps shown in FIG. 8G.

For each of these ingredients, the module or algorithm will further reduce the raw data that has already been filtered by the allergies, only this time it will filter by the column labeled "Category" (there are many varying food categories within the data). For example, in the selection of the bread to be used on the aforementioned sandwich, the module or algorithm will create another instance of the matrix of data that is then filtered based on the "Category" column to retain items of the category "Breakfast Sandwich Bread" or "Breakfast Sandwich Toast". Now from this further reduced matrix of breads and toasts, a single element is chosen at random to be the bread that is used in this meal.

Figure 8H:
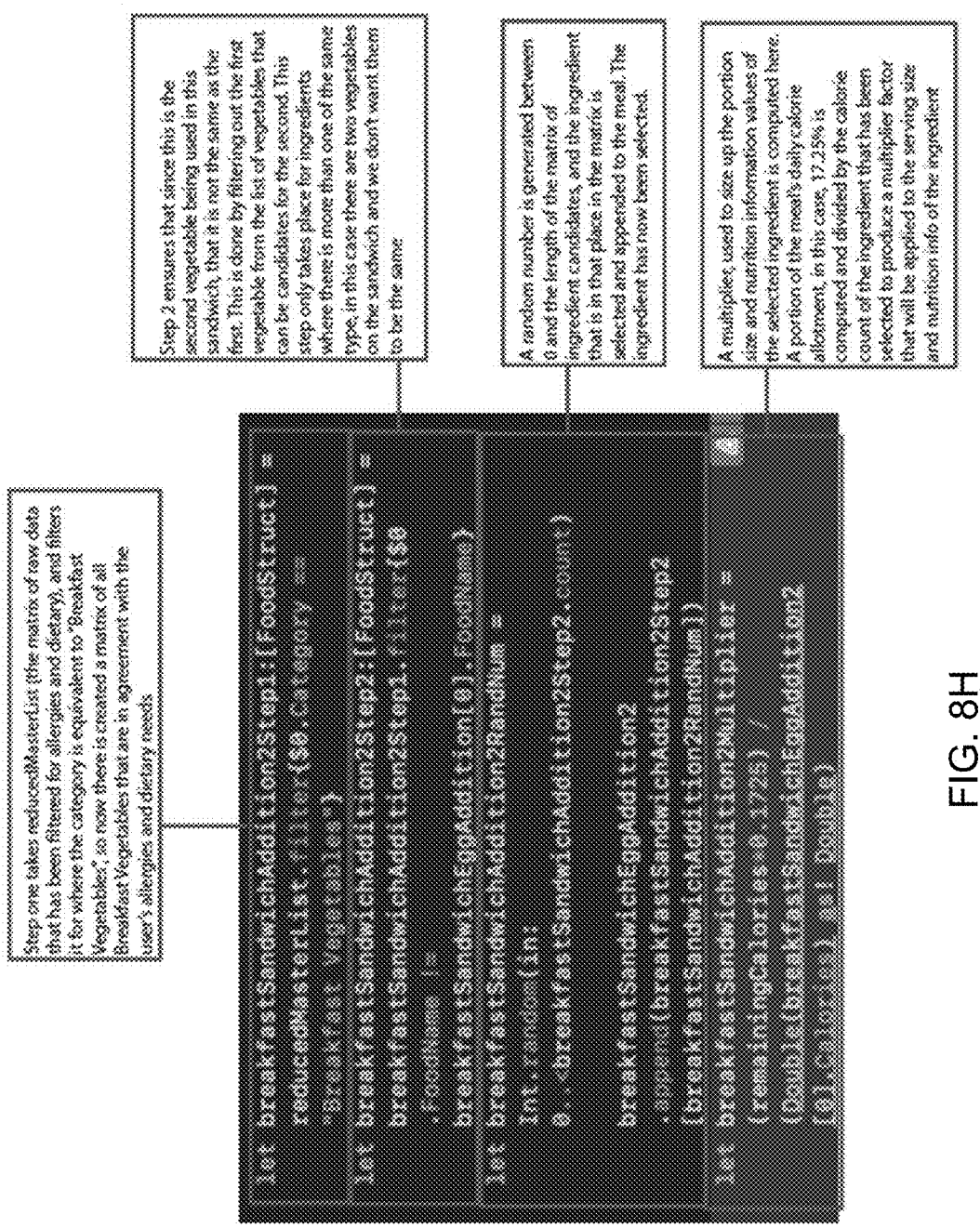

In some embodiments, the module or algorithm includes programming code to greatly reduce the probability of the same ingredient appearing twice within the same meal. For instance, in meals where there are 2-4 vegetables or fruits (or any ingredient of the same type) in a certain meal, the ingredients chosen in sequence cannot match each other, meaning Vegetable 2 cannot match Vegetable 1, and Vegetable 3 cannot match either Vegetable 1 or Vegetable 2 and so on. An example of the second vegetable ingredient selection for a breakfast egg sandwich is depicted in FIG. 8H.

Now that the ingredients that make up the meal have been randomly chosen, arranged and appended in the proper order, the system 10 will compute the serving sizes for the individual ingredients. Each meal (Breakfast, Lunch, Dinner), as mentioned above has already been allocated a fixed portion of the user's estimated daily calorie intake that was determined by the system 10 in an earlier step. Of that calorie allotment made to the meal, certain fixed percentages of that amount are allocated to each ingredient of the Sub-Meal. Once each selected ingredient is allotted an amount of calories, the amounts of calories, the multiplier from the screenshot in FIG. 8H, will be used to size up the serving size and dictate the recommended amount of each ingredient to be included in the meal. The raw data, as shown in FIGS. 4A-4B, contains foods in small quantities, so that the module or algorithm may manipulate them to either increase or decrease their size. This is done to determine the estimated quantity and estimated nutrition information of each ingredient that should be included in the meal output. The illustration in FIG. 8I depicts some of the elements of the ingredient being sized up. The algorithm also uses the elements in the "Image Identifier" column in the raw data sample pictured in FIGS. 4A-4B, the ingredients chosen to reference images that are designed for depicting each food ingredient in order to be displayed in the output table.

Once these steps have been completed, the randomized meal output is organized and displayed for the use on the client computing device 20, for example, in a table format on the "Randomized Output" page, shown in FIG. 3C. The output meal, with each of its ingredients individually randomly selected and sized to fit the user's estimated caloric needs are displayed in a table, with the title of the meal generated at the top. On this page, there are a number of things that the user can manipulate. Firstly, the user may tap the down arrows in each individual table cell in order to inspect the estimated nutritional information of each individual ingredient, or the "Total Meal Nutrition". The user may also tap the "Reload" button beneath the table, which will prompt the system to re-run the algorithm beginning at the stage in which it pulls the data from the food database or server, and instantly repopulate the table with a new meal for the user. The user may refresh as many times as they like and the results will always be instantaneous (e.g., <1.0 sec.). If the user wishes to retain certain ingredients, but change others, the user may tap the lock buttons located in the individual ingredient table cells, preserving those ingredients, then tap the "Reload" button. This will rerun the algorithm, and instantly replace all ingredients on the table except for the ones the user has chosen to lock. FIG. 8J illustrates an exemplary reload process.

When the "Reload" button is engaged, the system will rerun the module or algorithm outlined above, keeping the same Sub-Meal, but just picking and sizing new ingredients. In FIG. 8J, "MealRandomizer" is the function to rerun and temporarily store a new meal. Now, depending on whether the lock button in the meal display table cell has been activated, a Boolean value stored in a variable named locationsForRerunTruncated will be read. If locked, then the corresponding value within locationsForRerunTruncated will be 1, and therefore that ingredient will not change, if 0, that ingredient will be replaced with the corresponding ingredient from the newly generated meal (mealReloaded), depicted in FIG. 8K.

If the user lands on a meal that they are satisfied with, the user may tap the "Add to Library" button on the output page (FIG. 3C). This button will save the meal to the device's core storage (e.g., local storage 22), and can simultaneously or alternatively save their meal to an online database (e.g., remote storage 50). After tapping that button, the user will be segued to the "Library" screen (FIG. 3D), where all of the curated meals previously saved on the user's client computing device 20 will be displayed, as well as the dates that they were saved will be displayed.

In FIG. 3D, the screenshot in the upper left hand corner depicts the "Library" screen. On the "Library" screen, the system provides the user with three main functions. The user can swipe to delete individual entries, as illustrated in the screenshot in the upper right, or they can delete all entries by tapping the "Delete All" button. Doing this will remove the chosen elements from the user's core data cache, and those elements will no longer display when the user visits the "Library" page. The user may also tap a saved meal in the table in order to inspect it and view total meal or individual ingredient nutritional information, similarly to the "Randomize Output" page. In a preferred embodiment, the system prevents the user from altering the meals at this stage.

Figure 5:
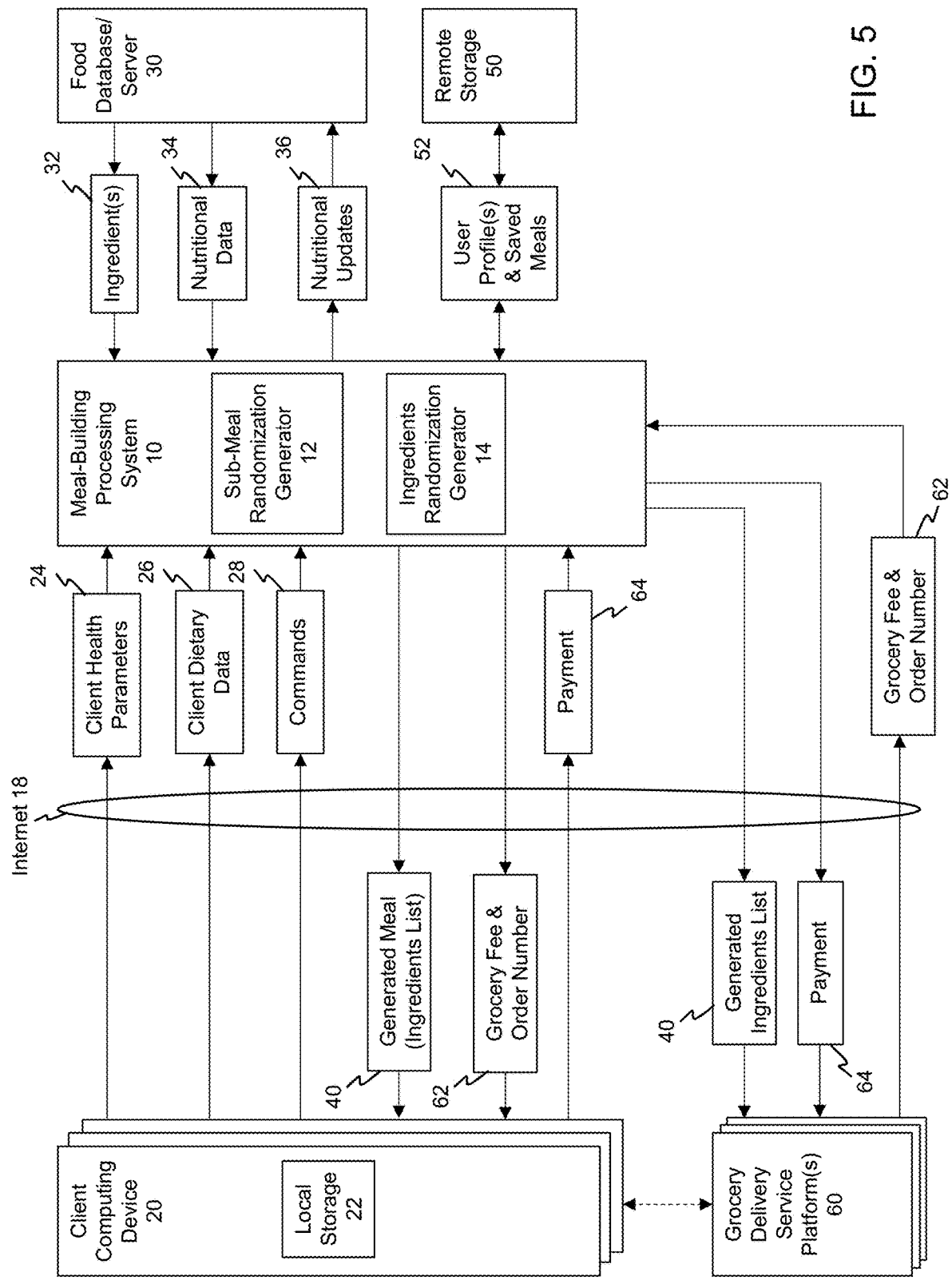
FIG. 5 is a block diagram of a meal-building system and/or application integrated with grocery delivery service system(s) or platform(s) according to the present teachings.

FIG. 5 shows another embodiment of the meal-building processing system or application 10. For example, the meal-building system 10 is connected to and interfaces with one or more grocery delivery service platforms 60 (e.g., Instacart, Shipt, PeaPod, FreshDirect, etc.) via the internet communication link 18. Once the meal-building system 10 generates the meal 40 (i.e., list of randomly selected sub-meal ingredients which satisfy the user's allergies, food preferences, and/or food aversions) with which the user is satisfied, the system 10 upon receiving a delivery order command from the client computing device 20 will transmit the meal 40 to a grocery delivery service platform 60 to prepare a shipment which includes one or more of the ingredients. The client computing device 20 or the system 10 may provide the grocery delivery service platform 60 with a delivery address. Further, the client computing device 20 may provide a preference for a particular grocery delivery service platform to use and/or particular grocery store (e.g., grocery chain, grocery store location) from which to obtain the ingredients. The grocery delivery service platform 60 will transmit the grocery fee information 62 (including processing fees, shipping and handling fees) to the meal-building processing system 10, which subsequently forwards this information to the client computing device 20. Thereafter, payment method and authorization data are transmitted from the client computing device 20 to the grocery delivery service platform 60 via the meal-building processing system 10. In response, the grocery delivery service platform 60 forwards an order number and shipping information (e.g., estimated date and time of delivery; tracking number) to the client computing device 20. In other embodiments, upon receiving a pick-up order command from the client computing device 20, the system 10 will transmit the meal 40 to a grocery service platform for a grocery store to retrieve one or more of the ingredients for pickup by the user. As one example, the client computing device 20 transmits the user's location (i.e., GPS coordinates) to the processing system 10 in order to determine the closest grocery store and transmit the pickup order to the proper grocery service platform associated with the closest grocery store. The grocery service platform will transmit the grocery fee information 62 (including service fees) to the meal-building processing system 10, which subsequently forwards this information to the client computing device 20. Once payment is received, the grocery delivery service platform 60 forwards an order number and pickup information (e.g., estimated time when pickup will be ready; pickup locker number, etc.) to the client computing device 20.

In some embodiments, there may be direct communication of the information/data 62 and 64 between the client computing device 20 and the grocery delivery service platform 60, as shown by the dashed line.

Figure 6:
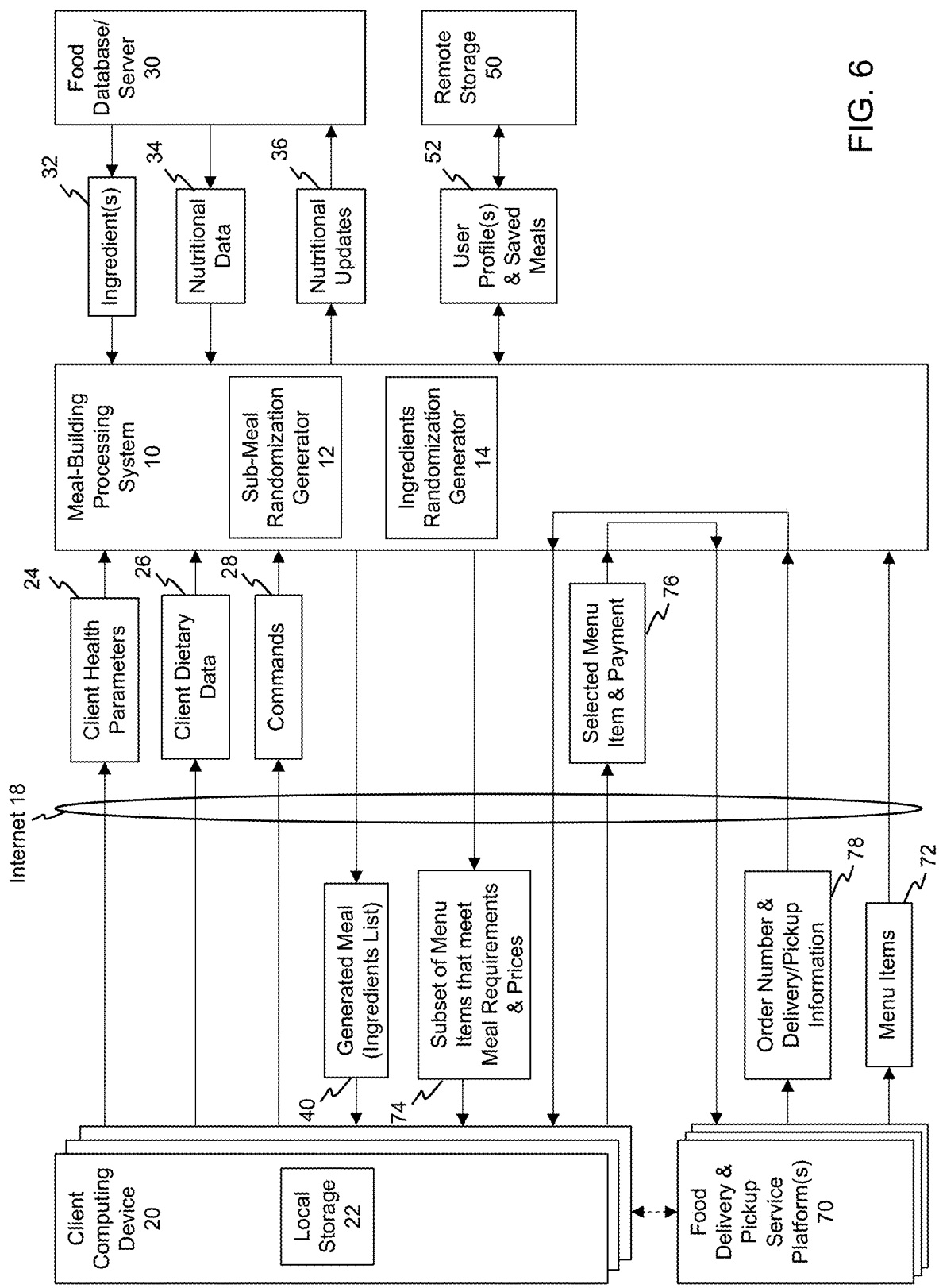
FIG. 6 is a block diagram of a meal-building system and/or application integrated with food delivery or take-out service system(s) or platform(s) according to the present teachings.

FIG. 6 shows another embodiment of the meal-building processing system or application 10. For example, the meal-building system 10 is connected to and interfaces with one or more food delivery and/or pickup service platforms 70 (e.g., UberEats, Grubhub, DoorDash, Seamless, ChowNow, OrderEm, Toast POS, etc.) via the internet communication link 18. Once the meal-building system 10 generates the meal 40 (i.e., list of randomly selected sub-meal ingredients which satisfy the user's allergies, food preferences, and/or food aversions) with which the user is satisfied, the system 10 upon receiving a food purveyor command from the user will retrieve a list of menu items 72 from a food delivery and/or pickup service platform 70 associated with the food purveyor (e.g., restaurant) selected by the user. The meal-building processing system 10 then analyzes the menu items and filters them according to the generated meal 40. A subset of the menu items 74 (which meet the meal requirements) and their corresponding prices 74 are transmitted from the meal-building processing system 10 to the client computing device 20. Thereafter, the meal-building processing system 10 is configured to receive a selected menu item(s) and payment information 76, which is subsequently forwarded to the delivery and/or pickup service platform 70. In response, the delivery and/or pickup service platform 70 transmits an order number and delivery/pickup information 78 (e.g., estimated time for delivery or pickup) to the client computing device 20. In some embodiments, there may be direct communication of the information/data 72-78 between the client computing device 20 and the delivery and/or pickup service platform 70, as shown by the dashed line.

Figure 7:
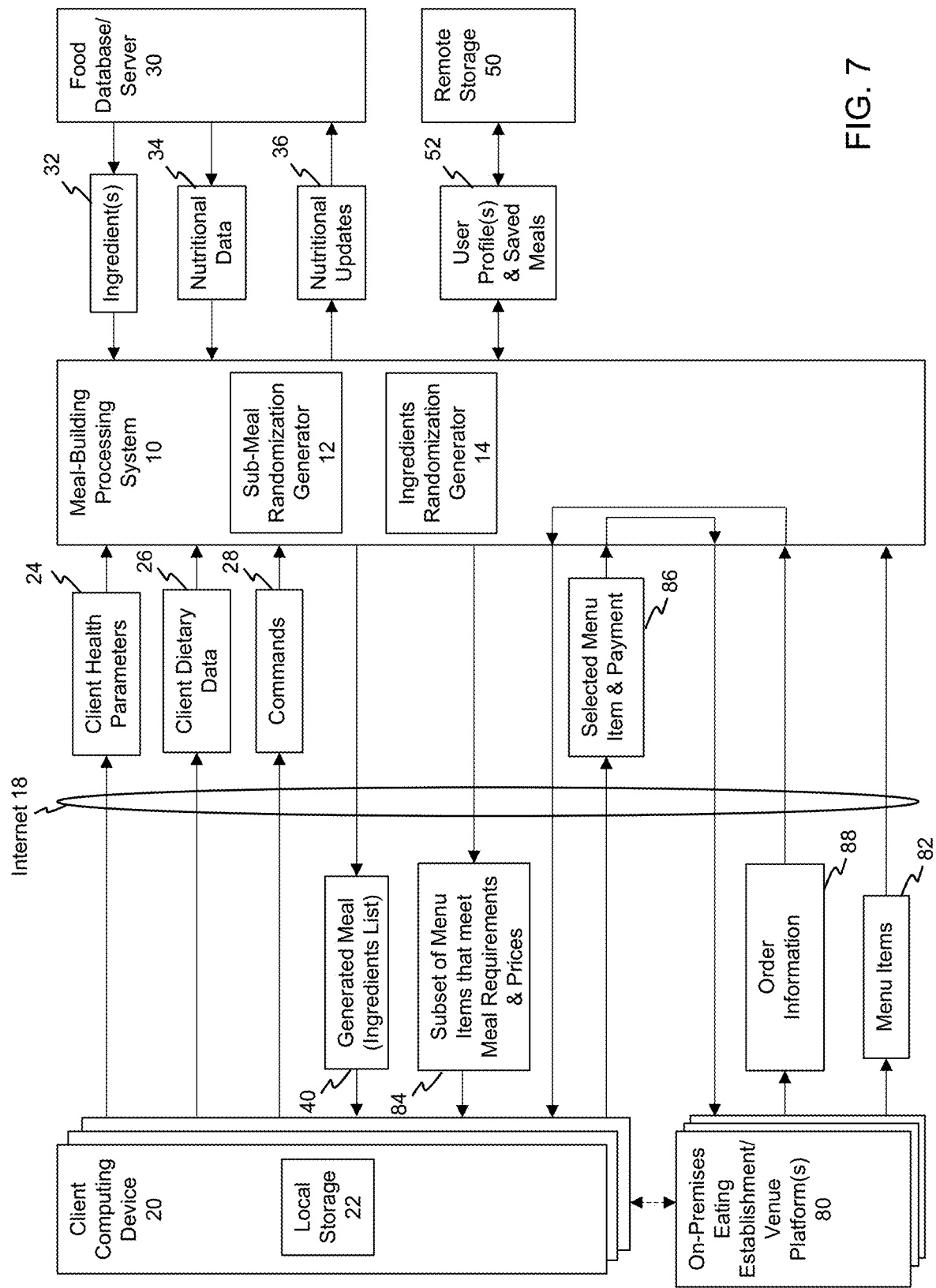
FIG. 7 is a block diagram of a meal-building system and/or application integrated with on-premises eating establishment/venue system(s) or platform(s) according to the present teachings.

FIG. 7 shows another embodiment of the meal-building processing system or application 10. For example, the meal-building system 10 is connected to one or more on-premises eating establishment/venue platforms 80 via the internet communication link 18. Once the meal-building system 10 generates the meal 40 (i.e., list of randomly selected sub-meal ingredients which satisfy the user's allergies, food preferences, and/or food aversions) with which the user is satisfied, the system 10 upon receiving a command from the user will retrieve a list of menu items 82 from an on-premises eating establishment/venue platform 80 associated with the on-premises eating establishment/venue selected by the user. The meal-building processing system 10 then analyzes the menu items and filters them according to the generated meal 40. A subset of the menu items 84 (which meet the meal requirements) and their corresponding prices 84 are transmitted from the meal-building processing system 10 to the client computing device 20. Thereafter, the meal-building processing system 10 is configured to receive a selected menu item(s) and payment information 86, which is subsequently forwarded to the on-premises eating establishment/venue platform 80. In response, the on-premises eating establishment/venue platform 80 transmits order information 88 to the client computing device 20. In some embodiments, there may be direct communication of the information/data 82-88 between the client computing device 20 and the on-premises eating establishment/venue platform 80, as shown by the dashed line.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. For example, in some instances, one or more features disclosed in connection with one embodiment can be used alone or in combination with one or more features of one or more other embodiments. It is intended that the scope of the present teachings should be determined by proper interpretation and construction of any claims and their legal equivalents, as understood by those of skill in the art relying upon the disclosure in this specification and the attached drawings.

What is claimed is:

1. A system for building a meal, comprising:
a processing device configured to generate a meal based on user health data and dietary data;
a client computing device positioned at a user location;
a communications link connecting the client computing device to the processing device for transmitting the user health data and dietary data;
a food database containing an archive of food ingredients and nutritional data; and
randomly-generated meal data comprising a subset of ingredients and nutritional facts for each ingredient in said subset;
the processing device having a sub-meal randomization generator and an ingredients randomization generator, wherein the sub-meal randomization generator is configured to randomly select a sub-meal based on a signal indicative of a meal type selected from the client computing device, wherein the ingredients randomization generator is configured to access the food database, filter the archive of food ingredients based on the dietary data to determine a set of ingredients, and randomly select from the set of food ingredients said subset of ingredients based on the sub-meal;
wherein the processing device retrieves the nutritional facts from the nutritional data stored in the food database and compiles the randomly-generated meal data for transmission to the client computing device; and
wherein the processing device is configured to receive a feedback signal from the client computing device allowing the user to accept or reject one or more of said subset ingredients, wherein the processing device re-initiates the sub-meal randomization generator and the ingredients randomization generator to create a new subset of ingredients that include the one or more accepted ingredients in response to said feedback signal and exclude the one or more rejected ingredients in response to said feedback signal.

2. The system according to claim 1, wherein the processing device is further configured to compute a daily calorie intake based on the user health data and allocates a portion of the daily calorie intake for the meal type selected from the client computing device based on fixed proportions.

3. The system according to claim 2, wherein the processing device determines the number of ingredients to include in said subset of ingredients according to the randomly-selected sub-meal.

4. The system according to claim 2, wherein the processing device applies predefined percentages to the allocated portion of the daily calorie intake to determine an amount of calories to be allotted to each subset ingredient.

5. The system according to claim 4, wherein upon determining the amount of calories to be allotted to each subset ingredient, the processing device uses a multiplier to calculate the serving size for each subset ingredient to be included in the meal.

6. The system according to claim 1, wherein the user health data obtained by the processing device comprises a current user weight, a user weight goal, and a date for achieving the user weight goal.

7. The system according to claim 6, wherein the user health data obtained by the processing device comprises medical conditions.

8. The system according to claim 6, wherein the user health data obtained by the processing device comprises measurements of user physical activity within a predefined period of time preceding meal generation; and
wherein the processing device includes a module that allots a portion of a computed daily calorie intake for the meal type selected based on said measurements of user physical activity.

9. The system according to claim 1, wherein the dietary data obtained by the processing device from the client computing device comprises allergy information, food aversions, and/or food preferences, wherein the ingredients randomization generator is configured to exclude ingredients associated with the allergy information and food aversions and is configured to promote inclusion of ingredients associated with the food preferences.

10. The system according to claim 9, wherein the processing device at least minimizes a probability of an ingredient appearing more than once in the subset of ingredients.

11. The system according to claim 1, wherein the nutritional data stored in the food database is updatable by the processing device based on food studies.

12. The system according to claim 1, wherein the processing device compiles the randomly-generated meal data in a table format prior to transmission to the client computing device.

13. The system according to claim 1, further comprising memory connected to the processing device to store the randomly-generated meal data, wherein the stored randomly-generated meal data is later accessible by the client computing device for viewing.

14. The system according to claim 1, wherein the communications link connects the processing device to a grocery service platform; and
wherein in response to a command from the client computing device, the processing device transmits the randomly-generated meal data to the grocery service platform for purchasing one or more of the subset of ingredients.

15. The system according to claim 14, wherein the command from the client computing device is a delivery command; and
wherein the processing device or the client computing device provides an address to the grocery service platform for delivering said one or more of the subset of ingredients and receives cost information and shipping information.

16. The system according to claim 14, wherein the command from the client computing device is a pickup command; and
wherein the processing device:
obtains a GPS position of the client computing device;
locates a grocery store in proximity to the GPS position;
transmits the randomly-generated meal data to the grocery service platform associated with the grocery store; and
receives cost information and pickup information from the grocery service platform.

17. The system according to claim 1, wherein the communications link connects the processing device to a food delivery service platform;
wherein in response to a command from the client computing device indicative of a food purveyor selected by the user, the processing device retrieves a list of menu items from the food delivery service platform associated with the selected food purveyor and filters the menu items that substantially match the randomly-generated meal data to form a subset of menu items, which are displayed on the client computing device.

18. A system for building a meal, comprising:

a processing device configured to generate a meal based on user health data and dietary data;

a client computing device positioned at a user location;

a communications link connecting the client computing device to the processing device for transmitting the user health data and dietary data;

a food database containing an archive of food ingredients and nutritional data; and randomly-generated meal data comprising a subset of ingredients and nutritional facts for each ingredient in said subset;

the processing device having a sub-meal randomization generator and an ingredients randomization generator, wherein the sub-meal randomization generator is configured to randomly select a sub-meal based on a signal indicative of a meal type selected from the client computing device, wherein the ingredients randomization generator is configured to access the food database, filter the archive of food ingredients based on the dietary data to determine a set of ingredients, and randomly select from the set of food ingredients said subset of ingredients based on the sub-meal;

the processing device retrieving the nutritional facts from the nutritional data stored in the food database and compiling the randomly-generated meal data for transmission to the client computing device;

wherein the processing device is configured to receive a feedback signal from the client computing device allowing the user to accept or reject one or more of said subset ingredients, wherein the processing device re-initiates the sub-meal randomization generator and the ingredients randomization generator to create a new subset of ingredients that include the one or more accepted ingredients in response to said feedback signal and exclude the one or more rejected ingredients in response to said feedback signal; and wherein the processing device is configured to transmit an order signal to an external service platform for purchasing one or more of the subset of ingredients or a meal having at least a majority of the subset of ingredients.

19. A system for building a meal, comprising:

a processing device configured to generate a meal based on user health data and dietary data;

a communications link connecting the processing device with a client computing device for receiving the user health data and dietary data from the client computing device;

a food database containing an archive of food ingredients and nutritional data; and randomly-generated meal data comprising a subset of ingredients and nutritional facts for each ingredient in said subset;

the processing device having a sub-meal randomization generator and an ingredients randomization generator, wherein the sub-meal randomization generator is configured to randomly select a sub-meal based on a signal indicative of a meal type selected from the client computing device, wherein the ingredients randomization generator is configured to access the food database, filter the archive of food ingredients based on the dietary data to determine a set of ingredients, and randomly select from the set of food ingredients said subset of ingredients based on the sub-meal;

wherein the processing device retrieves the nutritional facts from the nutritional data stored in the food database and compiles the randomly-generated meal data for transmission to the client computing device; and wherein the processing device is configured to receive a feedback signal from the client computing device allowing the user to accept or reject one or more of said subset ingredients, wherein the processing device re-initiates the sub-meal randomization generator and the ingredients randomization generator to create a new subset of ingredients that include the one or more accepted ingredients in response to said feedback signal and exclude the one or more rejected ingredients in response to said feedback signal.

* * * * *